(12) United States Patent
Zhang et al.

(10) Patent No.: US 9,772,306 B2
(45) Date of Patent: Sep. 26, 2017

(54) GAS ANALYZING APPARATUS AND SAMPLING DEVICE

(71) Applicant: NUCTECH COMPANY LIMITED, Beijing (CN)

(72) Inventors: Qingjun Zhang, Beijing (CN); Yuanjing Li, Beijing (CN); Zhiqiang Chen, Beijing (CN); Ziran Zhao, Beijing (CN); Yinong Liu, Beijing (CN); Yaohong Liu, Beijing (CN); Qiufeng Ma, Beijing (CN); Huishao He, Beijing (CN); Weiping Zhu, Beijing (CN); Xiang Zou, Beijing (CN); Jianping Chang, Beijing (CN); Song Liang, Beijing (CN)

(73) Assignee: NUCTECH COMPANY LIMITED, Beijing (CN)

( * ) Notice: Subject to any disclaimer, the term of this patent is extended or adjusted under 35 U.S.C. 154(b) by 0 days.

(21) Appl. No.: 15/115,217

(22) PCT Filed: Dec. 24, 2015

(86) PCT No.: PCT/CN2015/098665
§ 371 (c)(1),
(2) Date: Jul. 28, 2016

(87) PCT Pub. No.: WO2016/107484
PCT Pub. Date: Jul. 7, 2016

(65) Prior Publication Data
US 2016/0341695 A1 Nov. 24, 2016

(30) Foreign Application Priority Data
Dec. 31, 2014 (CN) .......................... 2014 1 0855715

(51) Int. Cl.
*G01N 27/00* (2006.01)
*G01N 27/62* (2006.01)
(Continued)

(52) U.S. Cl.
CPC .......... *G01N 27/622* (2013.01); *G01N 27/64* (2013.01); *G01N 30/30* (2013.01); *G01N 30/46* (2013.01);
(Continued)

(58) Field of Classification Search
CPC .... G01N 27/622; G01N 30/466; G01N 27/64; G01N 30/30; G01N 30/46; G01N 2030/3038
(Continued)

(56) References Cited

U.S. PATENT DOCUMENTS 5,808,178 A * 9/1998 Rounbehler ........... G01N 30/30
73/23.35
6,481,263 B1 * 11/2002 Haley .................. G01N 27/622
250/287
(Continued)

FOREIGN PATENT DOCUMENTS

| CN | 1296564 A | 5/2001 |
|---|---|---|
| CN | 1910453 A | 2/2007 |

(Continued)

OTHER PUBLICATIONS

International Search Report as issued in International Patent Application No. PCT/CN2015/098665, dated Mar. 29, 2016.
(Continued)

*Primary Examiner* — Michael Maskell
(74) *Attorney, Agent, or Firm* — Pillsbury Winthrop Shaw Pittman LLP (57) ABSTRACT

The present invention discloses a gas analyzing apparatus and a sampling device. The gas analyzing apparatus includes
(Continued)

a sampling device and an ion mobility spectrum analysis device. The sampling device includes a multi-capillary column and a temperature control system. The ion mobility spectrum analysis device is adapted for analyzing a gas leaded-in by the sampling device and includes a reaction cavity for reaction between sample molecules and reaction ions, the cavity having a sampling opening for leading-in of the gas. An outlet end of the multi-capillary column is inserted directly into the cavity of the ion mobility spectrum analysis device through the sampling opening of the ion mobility spectrum analysis device.

20 Claims, 3 Drawing Sheets (51) Int. Cl.
*G01N 27/64* (2006.01)
*G01N 30/30* (2006.01)
*G01N 30/46* (2006.01)

(52) U.S. Cl.
CPC ... *G01N 30/466* (2013.01); *G01N 2030/3038* (2013.01)

(58) Field of Classification Search
USPC .......................................... 250/281, 282, 288
See application file for complete search history.

(56) References Cited

U.S. PATENT DOCUMENTS

| | | | |
|---|---|---|---|
| 2009/0114812 A1 | 5/2009 | Landgraf | |
| 2010/0089811 A1* | 4/2010 | Zelechonok | G01N 30/606 210/198.3 |
| 2013/0009053 A1 | 1/2013 | Wu | |
| 2013/0180405 A1 | 7/2013 | Currie et al. | |
| 2014/0151546 A1 | 6/2014 | Li et al. | |
| 2015/0185190 A1 | 7/2015 | Zhang et al. | |
| 2016/0341695 A1 | 11/2016 | Zhang et al. | |

FOREIGN PATENT DOCUMENTS

| | | |
|---|---|---|
| CN | 101382526 A | 3/2009 |
| CN | 101728208 A | 6/2010 |
| CN | 201917559 U | 8/2011 |
| CN | 203798779 U | 8/2014 |
| CN | 104020237 A | 9/2014 |
| CN | 104515824 A | 4/2015 |
| CN | 204389459 U | 6/2015 |
| CN | 204424206 U | 6/2015 |
| CN | 104749264 A | 7/2015 |
| JP | S64-79652 A | 3/1989 |
| JP | 2000-509487 A | 7/2000 |
| JP | 2000-314731 A | 11/2000 |
| JP | 2002-503808 A | 2/2002 |
| JP | 2003-045451 A | 2/2003 |
| JP | 2007-518997 A | 7/2007 |

OTHER PUBLICATIONS

Office Action as issued in Chinese Patent Application No. 201410855715.5, dated Sep. 11, 2015.
Sielemann, S., et al., "Detection of trans-1,2-dichloroethene, trichloroethene and tetrachloroethene using Multi-Capillary Columns Coupled to Ion Mobility Spectrometers with UV-Ionisation Sources," International Journal for Ion Mobility Spectrometry, vol. 2, No. 1, Dec. 31, 1999, pp. 15-21.
Baumbach J.I., et al., "Coupling of Multi-Capillary Columns with two Different Types of Ion Mobility Spectrometer," International Journal for Ion Mobility Spectrometry, vol. 3, No. 1, Dec. 31, 2000, pp. 28-37.
Márquez-Sillero, I., et al., "Direct determination of 2,4,6-tricholoroanisole in wines by single-drop ionic liquid microextraction coupled with multicapillary column separation and ion mobility spectrometry detection," Journal of Chromatography A, 1218 (2011), pp. 7574-7580.
Non-Final Office Action as issued in Japanese Patent Application No. 2016-548034, dated May 15, 2017.
Sielemann, S., et al., "Detection of trans-1, 2-dichloroethene, trichloroethene and tetrachloroethene using Multi-Capillary Columns Coupled to Ion Mobility Spectrometers with UV-Ionisation Sources," International Journal for Ion Mobility Spectrometry (1999), pp. 15-21.

* cited by examiner

GAS ANALYZING APPARATUS AND SAMPLING DEVICE

This application is the U.S. national phase entry of PCT patent application no. PCT/CN2015/098665, which was filed on Dec. 24, 2015, which claims the benefit of priority of Chinese patent application no. 201410855715.5, which was filed on Dec. 31, 2014.

TECHNICAL FIELD

The present application relates to the field of safety detecting technology, and in particular, to a gas analyzing apparatus and a sampling device.

BACKGROUND

Currently, gas chromatography (GC) and ion mobility spectrometry (IMS) combination technology (GC-IMS) is used to pre-separate a sample, based on the prominent separating performance of GC for complex components, to separate a mixture into single components, and transfer them to an IMS detector for detection. It has been confirmed that such combination technology extends the resolution of IMS detection for chemical components by increasing the retention time information of GC, achieves higher detection limit and widens linear dynamic range. The GC-IMS combination technology has thus rapidly developed in recent years. However, a conventional GC analysis process has difficulty meeting the requirements of fast detection in situ as a complete GC analysis spends more than ten minutes and needs a huge oven to obtain high temperature conditions.

In addition, IMS is currently widely equipped with radioactive β source, which may radiate high-energy primary electron ($^{63}$Ni:67 keV, $^{3}$H:18 keV). The existing apparatus is configured to directly introduce a separated sample into an ionization area, where part of the sample is broken by the high-energy β ray into fragment ions, or is ionized as molecular ions with positive charge. On the one hand, the fragment ions may result in an increased wave crest of reactive ion (by monitoring RIP, it may be mainly $(H_2O)_nH^+$ in a positive mode, or it may be mainly $O_2^-(H_2O)_2$ in a negative mode), which may disturb a baseline and decrease resolution of IMS detection. Particularly, during detection of biomacromolecule such as protein molecular or nucleic acid, an electron ionization source will render more complex fragments, which will form a map that is hard to be identified. For this reason, it is difficult for a GC-IMS spectrometer to be applied in the field of detecting organic macromoleculars. On the other hand, the fragment ions or molecular ions with positive charge may be reacted with reactive ions to obtain an unresolvable ion spectrum, in which the lines in the spectrum are disordered and are troublesome to analyze. It is desired to provide accurate IMS detection.

SUMMARY

It is an object of the present invention to provide a gas analyzing apparatus, which at least partially overcomes or eliminates disadvantages, including inconvenient use, large volume and easy-introduced analytical error, of analyzing apparatuses in the prior art.

According to an aspect of the present invention, there is provided a gas analyzing apparatus, comprising: a sampling device and an ion mobility spectrum analysis device. The sampling device comprises: a multi-capillary column (MCC) consisted of a plurality of capillary columns and having an inlet end and an outlet end, and a temperature control system configured to couple with the multi-capillary column so as to control a temperature within the multi-capillary column. The ion mobility spectrum analysis device is adapted for analyzing a gas led in by the sampling device and comprises a reaction cavity for gas reaction between sample molecules and reaction ions, the reaction cavity having a sampling opening for leading in of the gas. The outlet end of the multi-capillary column is inserted directly into the reaction cavity of the ion mobility spectrum analysis device through the sampling opening of the ion mobility spectrum analysis device.

According to an aspect of the present invention, there is provided sampling device for a gas analyzing apparatus, comprising: a multi-capillary column consisted of a plurality of capillary columns formed of non-metallic material and having an inlet end and an outlet end, and a temperature control system configured to couple with the multi-capillary column so as to control a temperature within the multi-capillary column, the temperature control system having a thermal conductor casing. The thermal conductor casing comprises a plurality of protrusions on an outer circumference of the thermal conductor casing, the plurality of protrusions being configured to define spaces there among in which fluid passages are arranged or through which a fluid passes.

The gas analyzing apparatus of the present invention may achieve at least the following advantages:

1) Components separated by the multi-capillary column are guided directly into the reaction region in the middle of the dual-mode migration tubes (i.e. at the same time has a positive mode migration tube and a negative mode migration tube respectively analyzing cations and anions), instead of into the ionization region, which achieves the purpose of avoiding generation of fragment ions, and also enables the GC-IMS to identify positive and negative ions. As a result, the spectrometer is able to be responsive to both positive and negative electrical affinity of macromolecules, which makes up for shortcomings of prior art technologies and broadens the range of materials selectable for detection by the multi-capillary column-IMS device.

2) No switching element is required for interfaces of the multi-capillary column-IMS device, and the ports of the multi-capillary column are coupled directly with the IMS device, which avoids turbulent flow induced due to turn around of the switching element, and effectively improves detection sensitivity and resolution rate of the IMS device. Between the multi-capillary column and a reaction region base of the IMS device may be provided a thermal insulation positioning device, which has both positioning and thermal insulation functions, is simple in structure, and is easy to be mounted and operated, thereby avoiding additional provision of the switching element and a temperature control system design therefor.

3) The heating elements of the multi-capillary column are embedded evenly within the thermal conductor casing, and the benefits of this design are that rapid heating of the multi-capillary column is achieved, uniform heating of the multi-capillary column is ensured, the sample gasification and separation are ensured and separation discrimination is reduced.

4) A plurality of protrusions are provided on the thermal conductor casing such that heat radiating conduits may be embedded and wrapped in spaces among the plurality of protrusions. The coolant flowing within the conduits may bring heat away to quickly cool the multi-capillary column, which is useful for the multi-capillary column-ion mobility spectrum analysis device to quickly cope with variations in boiling point of the matter when performing a next measurement during a successive measurement period.

5) Cooperation and control of the thermal conductor casing, heat radiating conduits, heating elements, pumps and controllers achieve a programmed heating effect of the multi-capillary column. The application field of the multi-capillary column-ion mobility spectrum analysis device combined spectrometer can be extended to cope with separation of components of samples in a wide range of boiling points, which improves selective range of the substances to be analyzed.

DETAILED DESCRIPTION OF THE EMBODIMENTS

Although the present invention is subject to various modifications and alternatives, exemplary embodiments of the present invention will be shown in the attached drawings and be described in the description in detail as examples. It should be understood that, however, the attached drawings and the detailed description are not intended to limit the present invention the embodiment set forth herein, rather, are intended to cover all the modifications, equivalents and alternatives fallen into the principles and spirit of the present invention, the scope of which is defined in the claims. The attached drawings are provided for illustration purpose, and are not drawn to scale.

Several embodiments of the present invention will be explained hereafter with reference to the attached drawings.

Figure 1:
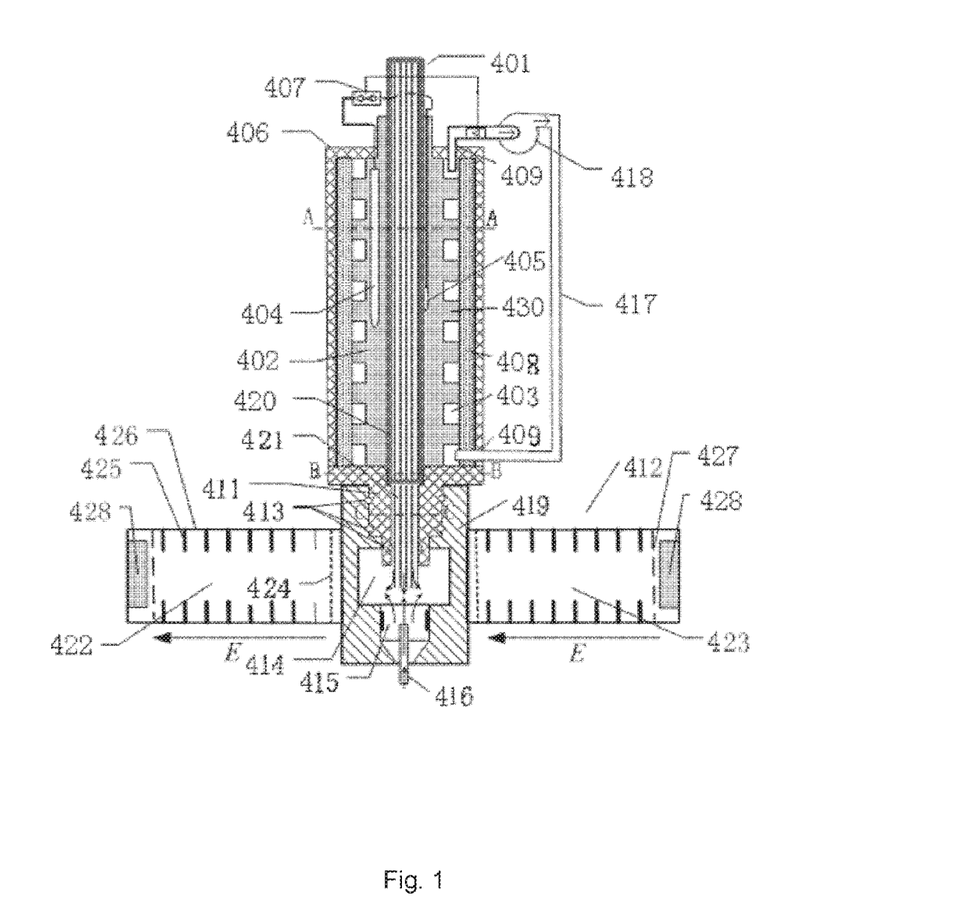
FIG. 1 is a schematic sectional view of a gas analyzing apparatus according to an embodiment of the present invention.

FIG. 1 is an overall structural schematic view of an embodiment of a gas analyzing apparatus 400 according to the present invention. The gas analyzing apparatus 400 may generally comprise a sampling device and an ion mobility spectrum analysis device.

The sampling device includes: a multi-capillary column 401 that comprises a plurality of capillary columns. In one embodiment, the multi-capillary column 401 may be formed by clustering a plurality of independent capillary columns in parallel into a bundle. In one embodiment, the multi-capillary column 401 may be formed by defining a plurality of capillary pores in parallel in one column. In one embodiment, the multi-capillary column 401 may be formed of non-metallic material. For example, generally, the capillary column may be formed of glass material. The capillary column may be also formed of other materials. The multi-capillary column 401 is configured to have an inlet end and an outlet end substantially aligned with each other. A multi-capillary column is consisted of hundreds of capillary columns in parallel. For example, 500~5000 capillary columns, each having an inner diameter of 20~100 μm, preferably of about 40 μm, in parallel are clustered within a glass column having a cross-section of regular hexagon. Each of the capillary columns is coated with a layer of stationary phase on its inner surface. Any types of stationary phase can be used depending on the demands. Due to its great separation ability, the multi-capillary column 401 is generally formed in a form of a pen-shaped column having relatively shorter size (of 40~250 mm), to achieve the separation function. A column having a relatively greater size may be coiled into a disc. Components of the mixed sample interact with the stationary phases of the capillary columns for different retention times so as to be separated from one another. Retention times for these capillary columns are in order of magnitude of seconds to minutes (generally, tens of seconds to several minutes, and the minimum peak width is several seconds).

The structure of the multi-capillary column 401 has the following advantages. Firstly, thousands of capillary columns are clustered so that the multi-capillary column 401 has greater capacity, which makes it have a greater sensitivity. Secondly, the capillary column in the multi-capillary column 401 is much finer in diameter, for example, the capillary column's inner diameter may be 20~100 μm, while a conventional capillary column has an inner diameter of 0.25~0.53 mm, that is, these capillary columns in the multi-capillary column 401 have greater separation effect, thus shorter capillary columns may achieve a better separation effect. Thirdly, the pen-shaped multi-capillary column 401 (of 40~250 mm) has less pressure gradients than conventional capillary columns (generally of 30 m), so the flow rate through the multi-capillary column 401 is greater than 2-3 orders of magnitude than that through conventional capillary columns, and may have a greater flow-rate range (of 20~150 ml/min). Accordingly, the multi-capillary column 401 enables not only fast separation but also isothermal separation. With the above advantages, on the one hand, the multi-capillary column-IMS provides an ability of approximately real-time separation and detection, and on the other hand, the multi-capillary column having shorter size helps to achieve a portable multi-capillary column-IMS.

In order to strengthen protection of the glass columns, enhancing the whole strength of the multi-capillary column and preventing them from accidentally cracking, the sampling device further comprises a metallic sleeve 420 configured to enclose and protect the multi-capillary column 401. FIG. 1 of the present disclosure shows a situation in which one metallic sleeve 420 is coupled around a regular hexagonal glass column, that is, the pen-shaped multi-capillary column 401 has a cross-section of a regular hexagon. The multi-capillary column 401 may have a cross-section of any other shape, e.g., circular.

The sampling device further comprises a temperature control system configured to couple with the multi-capillary column 401 so as to control a temperature within the multi-capillary column 401.

Specifically, the temperature control system of the sampling device comprises a thermal conductor casing 402 configured to be in a direct contact with the metallic sleeve 420 by which the multi-capillary column 401 is enclosed. The temperature control system further comprises at least one heater 404 and at least one sensor 405 embedded within the thermal conductor casing 402. Cooperation of the at least one heater 404 and the at least one sensor 405 may achieve control of a temperature of the thermal conductor casing 402. Various types of heaters may be used. For example, a plurality of heating rods 404, i.e., one or more heating rods 404 are embedded in the thermal conductor casing 402, is provided. The plurality of heating rods 404 may be distributed uniformly within the thermal conductor casing 402, so as to increase rapidly and evenly the temperature of the thermal conductor casing 402. FIG. 1 shows a situation in which one heating rod is used. Heating filaments may be embedded in the thermal conductor casing 402 and arranged to facilitate the uniform heating. For example, the thermal conductor casing 402 itself may be a kind of heating element for heating up.

In one embodiment, the sensor 405 may be provided adjacent to the metallic sleeve 420, so that the temperature measured by the sensor 405 is much closer to the temperature within the capillary columns. A plurality of the sensors 405 may be distributed uniformly with the thermal conductor casing 402 around the metallic sleeve 420.

Figure 2:
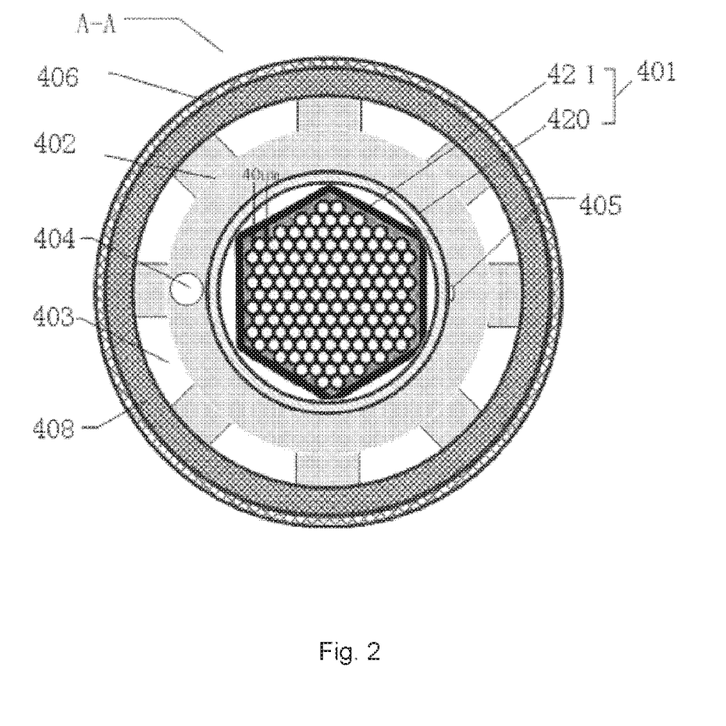
FIG. 2 is a sectional view of a gas analyzing apparatus according to an embodiment of the present invention along a line A-A.

In one embodiment, the thermal conductor casing 402 comprises a plurality of protrusions 430 on an outer circumference of the thermal conductor casing 402 and spaces 403 defined among the plurality of protrusions 430. These spaces may serve as grooves 403, or as fluid passages 403 through which a fluid passes, as shown in FIG. 2.

The sizes of these protrusions 430 may be the same as or different from one another. Spacings between adjacent protrusions 430 may be the same as or different from one another. For example, some of the protrusions 430 have relative greater size(s) while the rest of the protrusions 430 have relative smaller size(s). For example, if every two columns of protrusions 430 constitute a group, the spacing between every two groups of protrusions 430 is greater than that between two columns of protrusions 430 in each of the two groups. Also, the protrusions 430 may be arranged non-uniformly. It should be understood for those skilled in the art that the protrusions 430 may have other sizes and spacings and also may be arranged in other manners.

In other words, the thermal conductor casing 402 may be regarded as including two portions, one is a base of the thermal conductor casing 402 while the other one is a protrusion 430 of the thermal conductor casing 402. In one embodiment, the base may have a relatively smaller radial thickness, and the protrusion 430 may have a relatively greater height. Provision of the plurality of protrusions 430 on the thermal conductor 402 helps the fluid to flow among the protrusions 430, so as to exchange heat with the thermal conductor casing 402. In one embodiment, for example, gas is introduced and flows among the plurality of protrusions 430, accelerating heat exchange between the plurality of protrusions 430 on the thermal conductor casing 402 and the introduced gas. Here, the plurality of protrusions 430 can serve as heat sinks. In one embodiment, conduits through which the fluid passes may be wound around the plurality of protrusions 430. By heat exchange between high-temperature fluid or low-temperature fluid within the conduits and the thermal conductor casing 402, the temperature of the thermal conductor casing 402 is controllable.

In one embodiment, the base of the thermal conductor casing 402 has a relatively smaller thickness, and a heating film is disposed among the plurality of protrusions 430 and is configured for heating up the thermal conductor casing 402. Meanwhile, heat medium fluid conduits are disposed among the plurality of protrusions 430, to achieve a drop in temperature via thermal transmission. With this arrangement in combination with the sensors 405, the temperature of the thermal conductor casing 402 may be controlled rapidly.

Figure 4:
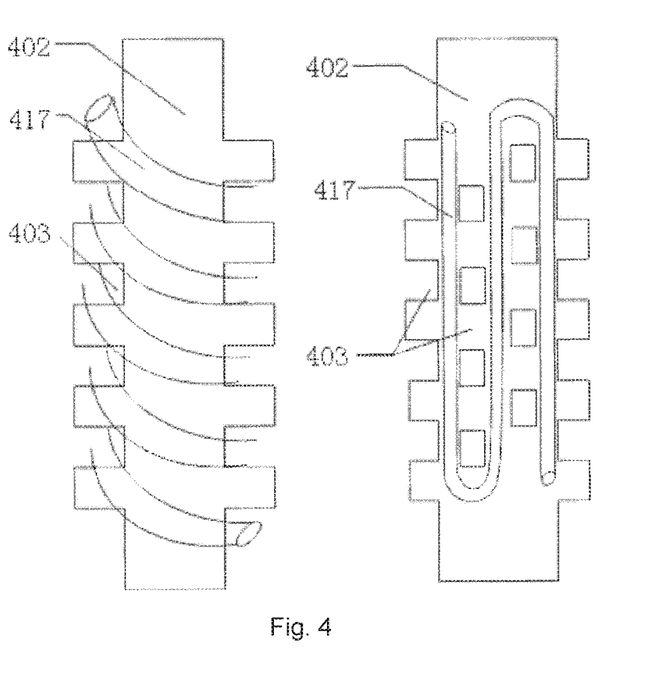
FIG. 4 shows an arrangement of a plurality of protrusions on a thermal conductor and fluid conduits located between the plurality of protrusions of a gas analyzing apparatus according to an embodiment of the present invention.

With the arrangement of the plurality of protrusions 430, the thermal conductor casing 402 has trenches where flowing heat medium fluid or heat medium fluid conduits are received, for thermal transmission. Specifically, FIG. 4 shows a situation where fluid conduits are wound among the plurality of protrusions 430. The heat medium fluid conduits may sinuously extend among the plurality of protrusions 430, or the heat medium fluid conduits are spirally located around the plurality of protrusions 430 of the thermal conductor casing 402, so that a thermal transmission is implemented between the heat medium fluid conduits and the thermal conductor casing 402. It should be understood that the fluid conduits may be arranged in the passages or trenches defined by the plurality of protrusions 430 in any manner; here, the protrusions 430 not only are used to implement heat exchange with the heat medium fluid conduits, but also act to support the conduits.

In one embodiment, provision of the plurality of protrusions 430 is advantageous. The plurality of protrusions 430 may be regarded as thermal dissipation protrusions 430 where heat is taken away directly by fluid. The plurality of protrusions 430 may be used as an arrangement for defining fluid passages among the plurality of protrusions and for fixation of the fluid passages.

In another embodiment of the present invention, the sampling device may further comprise a housing 406 enclosing the temperature control system. In one embodiment, the sampling device may further comprise a thermal insulation layer 408 disposed between the housing 406 and the thermal conductor casing 402. In one embodiment, the housing 406 may enclose around the outer surface of the thermal conductor casing 402 in a sealing manner. When the thermal conductor casing 402 is enclosed by the thermal insulation layer 408 and the housing 406, the plurality of protrusions on the thermal conductor casing 402 may be used to support the thermal insulation layer 408 and the housing 406. As shown in FIG. 1, a plurality of passages is formed between the plurality of protrusions and the thermal insulation layer 408. Heat medium fluid conduits may be arranged at the outer circumference of the thermal conductor 402 to pass through these passages or the abovementioned trenches, to enable sufficient thermal transmission.

In one embodiment, an air pump 418 may be provided to communicate with the abovementioned trenches 403 through conduits 417. Through the conduits 417, pressured gas is pumped by the air pump 418 into the trenches 403 among the plurality of protrusions 430, facilitating cooling or heating up of the thermal conductor casing 402. In one embodiment, fluid may be introduced directly into the trenches formed among the plurality of protrusions 430, for heat exchange.

In one embodiment, the inlet end of the multi-capillary column 401 extends out of the housing 406 of the sampling device to a feeder. A portion of the metallic sleeve 420, along with the multi-capillary column 401, may also extend out of the housing 406.

Since a flow velocity of the sample in the multi-capillary column 401 is greater than a conventional capillary column, interfaces of the sampling device and the ion mobility spectrum analysis device are particularly important. The interfaces of the sampling device with the ion mobility spectrum analysis device functions to introduce smoothly, without any quality degradation, the sample separated rapidly from the multi-capillary column 401 into the reaction region of the ion mobility spectrum analysis device.

In one embodiment, the gas analyzing apparatus 400 further comprises a thermal insulation positioning device 411 located on a reaction region base 419 and configured for connection between the sampling device and the ion mobility spectrum analysis device, and for isolating a thermal transmission between the sampling device and the ion mobility spectrum analysis device, so that the sampling device and the ion mobility spectrum analysis device are independently controlled respectively in terms of temperature.

Figure 3:
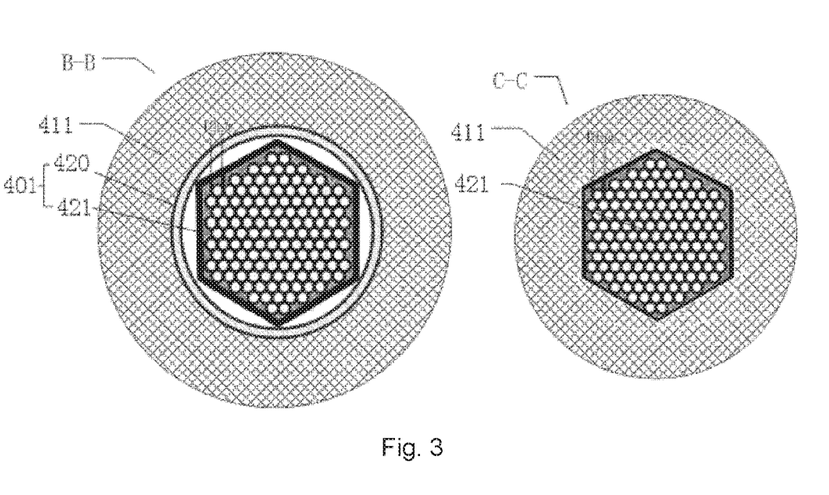
FIG. 3 is a sectional view of a gas analyzing apparatus according to an embodiment of the present invention along a line B-B and a line C-C.

In one embodiment, the thermal insulation positioning device 411 comprises a first connection end connected to the outlet end of the sampling device, and a second connection end connected to the ion mobility spectrum analysis device. Specifically, the first connection end is connected and sealed at one end of the multi-capillary column. The second connection end has a shape that complements a shape of an opening in the reaction region base 419 of the ion mobility analysis device. The shape of the thermal insulation positioning device 411 is shown in the cross-sectional views of FIG. 1 and FIG. 3. The thermal insulation positioning device 411 has a stepped shape, and, FIG. 3 shows the cross-sectional views along line B-B and line C-C, respectively. In one embodiment, a gasket may be provided on an outer surface of a section of the thermal insulation positioning device 411. The gasket 413 may act in a sealing function. When the sampling device is inserted into the ion mobility spectrum analysis device, the thermal insulation positioning device 411 is connected therebetween. So, a good sealing is necessary to avoid leakage of the particles within the reaction region 414 or to prevent ambient gas from entering the reaction region 414 to adversely affect accuracy of the measurement.

The thermal insulation positioning device 411 may be made of a plastic material, for example, PEEK, or Teflon. The thermal insulation positioning device 411 may be made of another non-metallic material having high temperature resistant performance and thermal insulation performance. For example, it can be made of a material such as refractory material, asbestos or the like. With the thermal insulation positioning device 411, the outlet end of the multi-capillary column 401 made of non-metallic material is inserted directly into a reaction cavity of the ion mobility spectrum analysis device, namely, into the reaction region 414 of the ion mobility spectrum analysis device, through a sample leading in opening of the ion mobility spectrum analysis device. Meanwhile, the metallic sleeve 420 is prevented from being close to the ionization region of the ion mobility spectrum analysis device, avoiding the metallic sleeve 420 from interfering with a zero electric field in the ionization region. Specifically, the metallic sleeve 420 is kept out of the sample leading in opening of the ion mobility spectrum analysis device. Preferably, the metallic sleeve 420 is kept away from the sample leading in opening of the ion mobility spectrum analysis device.

With this arrangement, the sample is fed directly into the reaction region 414 of the ion mobility spectrum analysis device, avoiding the problem in the prior art that gaseous material introduced into the ionization region 415 is broken, e.g., by high-energy ray beams, into ion fragments. Meanwhile, the gaseous material can be separated by the capillary columns, for meeting analytical requirements, and is fed into the reaction region 414, for analysis.

In one embodiment, the thermal insulation positioning device 411 may be integrated with the sampling device, which is advantageous in practice. In this case, one end of the sampling device is sealed up by the thermal insulation positioning device 411, while the outlet end of the sampling device runs out of the thermal insulation positioning device 411, as shown in FIG. 1. Here, the outlet end of the sampling device including the thermal insulation positioning device 411 is shown in FIG. 1. That is, the multi-capillary column 401 is wrapped by the end of the thermal insulation positioning device 411 and a part of the multi-capillary column is directly wrapped by the non-metallic material of the thermal insulation positioning device 411.

The arrangement of the thermal insulation positioning device 411 enables a convenient and direct insertion of the sampling device into the reaction cavity, namely the reaction region 414, of the ion mobility spectrum analysis device. It is especially important in a situation where a rapid analysis of the gas sample is required. The sampling device may be temperature-controlled independently. The temperature of the sampling device may be controlled independently in a preparation time. When the sampling device is at a desired temperature condition, it is inserted into the ion mobility spectrum analysis device. Connection and relative positions between the sampling device and the ion mobility spectrum analysis device are achieved by use of the thermal insulation positioning device 411. Due to thermal insulation property and rigidity of the thermal insulation positioning device 411, accuracy of the measurement of the ion mobility spectrum analysis device will not be affected by the temperature of the sampling device, and a positional relationship between the sampling device and the ion mobility spectrum analysis device may be determined. With this arrangement, connection and disconnection between the sampling device and the ion mobility spectrum analysis device may be implemented conveniently, which has a positive significance in the practical inspection process, greatly facilitates inspection of different samples, facilitates transportation, and achieves a reduced volume of the whole inspection system. For example, a plurality of sampling devices may be equipped, which facilitates inspection of different samples and increases speed and accuracy of the inspection.

In one embodiment, a length of the metallic sleeve 420 of the multi-capillary column 401 is configured so that the metallic sleeve 420 does not extend into the ionization region 415 of the ion mobility spectrum analysis device when the multi-capillary column 401 is inserted into the reaction cavity 414 of the multi-capillary column. The end of the metallic sleeve 420 is terminated in the thermal insulation positioning device 411, for example, at a position shown in FIG. 1. However, it should be noted that the location of the metallic sleeve 420 may be changed as long as the metallic sleeve 420 is kept out of the reaction region 414 where the ions are contained. For example, the metallic sleeve 420 is kept out of, or is kept away, from the sample leading in opening of the ion mobility spectrum analysis device.

In one embodiment, the gas analyzing apparatus 400 further comprises an ion mobility spectrum analysis device adapted for analyzing a sample led in by the sampling device. The ion mobility spectrum analysis device comprises a reaction cavity 414 for gas reaction between molecules of the sample and reaction ions, and the reaction cavity 414 has a sample leading in opening for lead in of the sample. The ion mobility spectrum analysis device further comprises an ionization region 415.

Referring to FIG. 1, the sampling device is positioned at an upper side of the ion mobility spectrum analysis device, and, the ionization region 415 is positioned at a lower side of the ion mobility spectrum analysis device. In one embodiment of the present invention, it is advantageous to arrange the sampling device to be opposed to the ionization region 415 of the ion mobility spectrum analysis device. Being different from the prior art technical concept that the sample is ionized after being introduced into the ionization region 415, the sampling device of the present invention is configured to keep the sample to be analyzed away from the ionization region 415 but to directly introduce the sample to be analyzed into the reaction region 414. It advantageously prevents generation of fragment ions, and avoids the problem in the prior art that the sample introduced into the ionization region 415 is broken into ion fragments, e.g., due to turbulence caused by non-linear gas passage. That is, the sample is introduced smoothly into the ion mobility spectrum analysis device while being separated rapidly.

In one embodiment of the present invention, the ion mobility spectrum analysis device 412 comprises positive and negative dual mode migration tubes 422, 423, the reaction region 414 is located between the positive mode migration tube 422 and the negative mode migration tube 423, and the ionization region 415 and the reaction region 414 are arranged separately and are communicated via an opening that can be closed and opened, as the arrangement shown in FIG. 1. For example, the ionization region 415 is located adjacent to a side of the reaction region 414.

In one embodiment in accordance with the design idea of the present invention, carrier gas 416 such as air is introduced into the ionization region 415, and is ionized in ionization region 415 to generate positive reaction ions $H^+(H_2O)_n$ and negative reaction ions $O_2^-(H_2O)_n$. The electrically charged reaction ions are transmitted into the reaction region 414 and collide with the sample molecules in the reaction region 414, so that the sample molecules are ionized to generate product ions. It is different from the prior art where the sample gas is ionized together with the carrier gas. For example, a bio-macromolecule is combined with a hydrated proton or hydrated oxygen ion to form molecules with positive or negative charge. The positive mode migration tube 422 and the negative mode migration tube 423 each comprises an ion gate 424, a migration area, a suppressor grid 427 and a Faraday disc 428. The migration area may be defined by stainless steel protective rings 425 and ceramic insulating rings 426 which are arranged in series. Sample particles with positive charge are detected in the positive mode migration tube, and sample particles with negative charge are detected in the negative mode migration tube.

Specifically, the carrier gas 416 is ionized in the ionization region 415 of the ion mobility spectrum analysis device to generate reactive ions. The reactive ions are swept, by the carrier gas 416 from the ion mobility spectrum analysis device, into the reaction region 414 through the carrier gas inlet of the ionization region 415. In the reaction region 414, the reactive ions encounter the sample separated by the multi-capillary column 401 to produce an electrophilic reaction of adsorption, so that the sample molecules adsorb the reactive ions to generate charged product ions, and the positive and negative charged product ions are guided into and separated in the positive mode migration tube 422 and the negative mode migration tube 423, respectively, with promotion by positive and negative electrical fields within the migration tubes, and are detected by the Faraday discs 428 at either end of the migration tubes. Other designs and principles of the ion mobility spectrum analysis device 412 are described in Chinese patent application No. 200810119974.6, the contents of which are incorporated herein by reference.

In an embodiment, there is provided a gas analyzing apparatus, comprising: a sampling device, comprising: a multi-capillary column consisted of a plurality of capillary columns and having an inlet end and an outlet end, and a temperature control system configured to couple with the multi-capillary column so as to control a temperature with the multi-capillary column; and an ion mobility spectrum analysis device adapted for analyzing a gas leaded-in by the sampling device and comprising a reaction cavity for gas reaction between sample molecules and reaction ions, the reaction cavity having a sampling opening for leading-in of the gas, wherein the outlet end of the multi-capillary column is inserted directly into the reaction cavity of the ion mobility spectrum analysis device through the sampling opening of the ion mobility spectrum analysis device.

In an embodiment, the gas analyzing device further comprises a thermal insulation positioning device configured for connection between the sampling device and the ion mobility spectrum analysis device, and for isolating a thermal transmission between the sampling device and the ion mobility spectrum analysis device, so that the sampling device and the ion mobility spectrum analysis device are independently controlled respectively in terms of temperature. In an embodiment, the thermal insulation positioning device comprises a first connection end connected to the outlet end of the sampling device and sealing upon an end of the multi-capillary column, and a second connection end connected to the ion mobility spectrum analysis device and having a shape that complements a shape of the opening of the reaction cavity of the ion mobility analysis device. In an embodiment, the thermal insulation positioning device is formed of a non-metallic material with high temperature resistance and thermal insulation performances. In an embodiment, the capillary columns are formed of non-metallic material. In an embodiment, the capillary columns have a diameter in a range from 40 μm to 100 μm. In an embodiment, the sampling device further comprises a metallic sleeve configured to enclose and protect the multi-capillary column, and a length of the metallic sleeve for the multi-capillary column is configured so that the metallic sleeve does not extend into the sampling opening of the ion mobility spectrum analysis device when the multi-capillary column is inserted into the cavity of the multi-capillary column. In an embodiment, the temperature control system of the sampling device comprises a thermal conductor casing configured to be in a direct contact with the metallic sleeve by which the multi-capillary column is enclosed, and at least one heater and at least one sensor being embedded within the thermal conductor casing. In an embodiment, the thermal conductor casing comprises a plurality of protrusions on an outer circumference of the thermal conductor casing, the plurality of protrusions being configured to define spaces there among in which fluid passages are arranged or through which a fluid passes. In an embodiment, heat medium fluid conduits go through the plurality of protrusions in a zigzag manner or in a manner that the heat medium fluid conduits go through the plurality of protrusions spirally around the thermal conductor, so that heat is transferred between the heat medium fluid conduits and the thermal conductor casing. In an embodiment, the sampling device further comprises a housing enclosing the temperature control system. In an embodiment, the sampling device further comprises a thermal insulation layer disposed between the housing and the thermal conductor casing. In an embodiment, the thermal insulation layer is supported by the plurality of protrusions on the thermal conductor casing. In an embodiment, the ion mobility spectrum analysis device is a positive and negative ion dual mode migration tube comprising a positive ion migration tube and a negative ion migration tube, and the ion mobility spectrum analysis device comprises an ionization region configured to ionize the led in carrier gas into reactive ions and feed the reactive ions to a reaction region, wherein the ionization region is provided at a side of the ion mobility spectrum analysis device opposite to the outlet end of the multi-capillary column.

In an embodiment, there is provided a sampling device for a gas analyzing apparatus, comprising: a multi-capillary column consisted of a plurality of capillary columns formed of non-metallic material and having an inlet end and an outlet end, and a temperature control system configured to couple to the multi-capillary column so as to control a temperature within the multi-capillary column, the temperature control system having a thermal conductor casing, wherein the thermal conductor casing comprises a plurality of protrusions on an outer circumference of the thermal conductor casing, the plurality of protrusions being configured to define spaces there among in which fluid passages are arranged or through which a fluid passes.

Although several exemplary embodiments of the present invention have been shown and described, it would be appreciated by those skilled in the art that various changes or modifications may be made in these embodiments without departing from the principles and spirit of the present invention, the scope of which is defined in the claims and their equivalents.

What is claimed is:

1. A gas analyzing apparatus, comprising:
   a sampling device, comprising:
      a multi-capillary column comprising a plurality of capillary columns and having an inlet end and an outlet end, and
      a temperature control system configured to couple with the multi-capillary column so as to control a temperature within the multi-capillary column; and
   an ion mobility spectrum analysis device configured to analyze a sample of gas led in by the sampling device and comprising a reaction cavity for gas reaction between sample molecules and reaction ions, the reaction cavity having a sampling opening for leading in of the gas,
   wherein the outlet end of the multi-capillary column is inserted directly into the reaction cavity of the ion mobility spectrum analysis device through the sampling opening of the ion mobility spectrum analysis device.

2. The gas analyzing apparatus according to claim 1, further comprising a thermal insulation positioning device configured for connection between the sampling device and the ion mobility spectrum analysis device, and for isolating a thermal transmission between the sampling device and the ion mobility spectrum analysis device, so that the sampling device and the ion mobility spectrum analysis device are independently controlled respectively in terms of temperature.

3. The gas analyzing apparatus according to claim 2, wherein the thermal insulation positioning device comprises a first connection end connected to the outlet end of the sampling device and sealing upon an end of the multi-capillary column, and a second connection end connected to the ion mobility spectrum analysis device and having a shape that complements a shape of the opening of the reaction cavity of the ion mobility analysis device.

4. The gas analyzing apparatus according to claim 2, wherein the thermal insulation positioning device is formed of a non-metallic material with high temperature resistance and thermal insulation performances.

5. The gas analyzing apparatus according to claim 1, wherein the capillary columns are formed of non-metallic material.

6. The gas analyzing apparatus according to claim 1, wherein the capillary columns have a diameter in a range from 40 μm to 100 μm.

7. The gas analyzing apparatus according to claim 1, wherein the sampling device further comprises a metallic sleeve configured to enclose and protect the multi-capillary column, and a length of the metallic sleeve for the multi-capillary column is configured so that the metallic sleeve does not extend into the sampling opening of the ion mobility spectrum analysis device when the multi-capillary column is inserted into the cavity of the multi-capillary column.

8. The gas analyzing apparatus according to claim 7, wherein the temperature control system of the sampling device comprises a thermal conductor casing configured to be in a direct contact with the metallic sleeve by which the multi-capillary column is enclosed, and at least one heater and at least one sensor embedded within the thermal conductor casing.

9. The gas analyzing apparatus according to claim 8, wherein the thermal conductor casing comprises a plurality of protrusions on an outer circumference of the thermal conductor casing, the plurality of protrusions being configured to define spaces there among in which fluid passages are arranged or through which a fluid passes.

10. The gas analyzing apparatus according to claim 9, wherein heat medium fluid conduits go through the plurality of protrusions in a zigzag manner or in a manner that the heat medium fluid conduits go through the plurality of protrusions spirally around the thermal conductor, so that heat is transferred between the heat medium fluid conduits and the thermal conductor casing.

11. The gas analyzing apparatus according to claim 1, wherein the sampling device further comprises a housing enclosing the temperature control system.

12. The gas analyzing apparatus according to claim 11, further comprising a thermal insulation layer disposed between the housing and a thermal conductor casing enclosing the multi-capillary column.

13. The gas analyzing apparatus according to claim 12, wherein the thermal insulation layer is supported by a plurality of protrusions on the thermal conductor casing.

14. The gas analyzing apparatus according to claim 1, wherein the ion mobility spectrum analysis device is a positive and negative ion dual mode migration tube comprising a positive ion migration tube and a negative ion migration tube, and the ion mobility spectrum analysis device comprises an ionization region configured to ionize the led in carrier gas into reactive ions and feed the reactive ions to a reaction region, wherein the ionization region is provided at a side of the ion mobility spectrum analysis device opposite to the outlet end of the multi-capillary column.

15. A sampling device for a gas analyzing apparatus, the sampling device comprising:
   a multi-capillary column comprising a plurality of capillary columns formed of non-metallic material and having an inlet end and an outlet end, and
   a temperature control system configured to couple to the multi-capillary column so as to control a temperature within the multi-capillary column, the temperature control system having a thermal conductor casing,
   wherein the thermal conductor casing comprises a plurality of protrusions on an outer circumference of the thermal conductor casing, the plurality of protrusions being configured to define spaces there among in which fluid passages are arranged or through which a fluid passes.

16. The sampling device according to claim 15, further comprising a housing enclosing the temperature control system and the thermal conductor casing.

17. The sampling device according to claim 16, further comprising a thermal insulation layer disposed between the housing and the thermal conductor casing.

18. The sampling device according to claim 17, wherein the thermal insulation layer is supported by the plurality of protrusions on the thermal conductor casing.

19. The sampling device according to claim 15, further comprising a metallic sleeve configured to enclose and protect the multi-capillary column, the thermal conductor casing enclosing the metallic sleeve.

20. The sampling device according to claim 15, further comprising a thermal insulation positioning device configured for connecting an ion mobility spectrum analysis device to the sampling device, and for isolating a thermal transmission between the sampling device and the ion mobility spectrum analysis device, so that the sampling device and the ion mobility spectrum analysis device are independently controlled respectively in terms of temperature.

* * * * *